(12) United States Patent
Sambandan et al.

(10) Patent No.: US 9,962,421 B2
(45) Date of Patent: May 8, 2018

(54) COMPOSITION COMPRISING CAFFEOYLSHIKIMIC ACIDS, PROTOCATECHUIC ACID, HYDROXYTYROSOL, HYDROXYBENZOIC ACID AND THEIR DERIVATIVES AND METHOD OF PREPARATION THEREOF

(71) Applicant: MALAYSIAN PALM OIL BOARD, Kajang, Selangor (MY)

(72) Inventors: T. G. Sambandan, Uxbridge, MA (US); ChoKyun Rha, Boston, MA (US); Anthony J. Sinskey, Boston, MA (US); Ravigadevi Sambanthamurthi, Selangor Darul Ehsan (MY); Yew Ai Tan, Kuala Lumpur (MY); Kalyana Sundram P. Manickam, Selangor Darul Ehsan (MY); Mohd Basri Wahid, Selangor Darul Ehsan (MY)

(73) Assignee: Malaysian Palm Oil Board, Kajang, Selangor (MY)

( * ) Notice: Subject to any disclaimer, the term of this patent is extended or adjusted under 35 U.S.C. 154(b) by 0 days. days.

(21) Appl. No.: 15/621,078

(22) Filed: Jun. 13, 2017

(65) Prior Publication Data
US 2017/0348373 A1    Dec. 7, 2017

Related U.S. Application Data

(62) Division of application No. 13/322,494, filed as application No. PCT/MY2010/000089 on May 26, 2010, now abandoned.

(30) Foreign Application Priority Data

May 26, 2009    (MY) .............................. PI 20092142

(51) Int. Cl.
*A61K 36/889*    (2006.01)
(52) U.S. Cl.
CPC .................................. *A61K 36/889* (2013.01)
(58) Field of Classification Search
CPC .................................................... A61K 36/889
USPC ............................................................ 560/75
See application file for complete search history.

(56) References Cited

U.S. PATENT DOCUMENTS

2003/0031740 A1    2/2003    Sambanthamurthi et al.

OTHER PUBLICATIONS

Ziouti et al. Biologia Plantarum (1996), 38(3), p. 451-457.*
Maier et al. J. Food Sci. (1965), 30, p. 747-752.*
T. Natishan J. of Liquid Chrom & Related Technologies, 27(7-9), p. 1237-1316.*
Vogel's textbook of practical organic chemistry, 5th ed, 1989; p. 209, "Liquid-Solid Column Chromatography".
International Search Report and Written Opinion from International Application No. PCT/MY2010/000089, dated Sep. 13, 2010.

* cited by examiner

*Primary Examiner* — Yong Chu
(74) *Attorney, Agent, or Firm* — Coeus Intellectual Property

(57) ABSTRACT

A composition comprising caffeoylshikimic acids, protocatechuic acid, hydroxytyrosol, hydroxybenzoic acid, caffeoylshikimic acids and their derivatives extracted from any part of oil palm including but not confined to the vegetation liquor of palm oil milling and palm oil mill effluent, and a method for use in the preparation of a composition containing caffeoylshikimic acids, protocatechuic acid, hydroxytyrosol, hydroxybenzoic acid, caffeoylshikimic acids and their derivatives. The method includes the steps of pre-concentrating an extract containing the caffeoylshikimic acids, protocatechuic acid, hydroxytyrosol, hydroxybenzoic acid, caffeoylshikimic acids and their derivatives and isolating said caffeoylshikimic acids, protocatechuic acid, hydroxytyrosol, hydroxybenzoic acid, caffeoylshikimic acids and their derivatives from said extract by liquid chromatography, wherein the elution activity of said caffeoylshikimic acids, protocatechuic acid, hydroxytyrosol, hydroxybenzoic acid, caffeoylshikimic acids and their derivatives vary depending on the stationary phase and the composition of the mobile phase.

5 Claims, 8 Drawing Sheets

Caffeoylshikimic acid (isomers are 5-O-R, 4-O-R, and 3-O-R)

4-Hydroxyl benzoate

Hydroxytyrosol

COMPOSITION COMPRISING CAFFEOYLSHIKIMIC ACIDS, PROTOCATECHUIC ACID, HYDROXYTYROSOL, HYDROXYBENZOIC ACID AND THEIR DERIVATIVES AND METHOD OF PREPARATION THEREOF

CROSS-REFERENCE TO RELATED APPLICATIONS

This application is a divisional of U.S. application Ser. No. 13/322,494 filed on Nov. 25, 2011, which is a National Stage Application of International Application No. PCT/MY10/00089 filed on May 26, 2010, which claims benefit of Malaysian Serial No. PI 20092142, filed May 26, 2009 in Malaysia, and which applications are incorporated herein by reference in their entireties. To the extent appropriate, a claim of priority is made to each of the above disclosed applications.

FIELD OF THE INVENTION

The present invention relates generally to a composition comprising at least 5 major compounds which include the isomers of caffeoylshikimic acid, para hydroxybenzoic acid protocatechuic acid and hydroxytyrosol and a method for preparing the same from oil palm including but not confined to the vegetation liquor of palm oil milling. This includes the separation and purification of caffeoylshikimic acid from the aqeous vegetation liquor.

BACKGROUND OF THE INVENTION

Shimikic acid and its derivatives, found naturally in some plants play a significant role as a biochemical intermediate compound in plants and also microorganisms. It is known to be an imperative precursor for the synthesis of aromatic amino acids, phenolics and alkaloids amongst many others. One of the most pertinent advancements in relation to the exploitation of shikimic acids in the pharmaceutical industry is the production of Tamiflu, a type of drug for use against avian flu in the recent years.

The demand for shikimic acid is expected to increase dramatically with the increase in world population and thus the need for various industrial and pharmaceutical uses e.g in the use of shikimic acid to manufacture tamiflu or other anti-viral drugs in the event of pandemic flu outbreak. At present, the world's demand for shimikic acid is met from fruits of Chinese star anise; however it is generally found in substantially low concentrations. The low availability of star anise has hampered the production of tamiflu and stresses the need for other sources of shikimic acid. Accordingly, it would be desirable to explore other sources for shikimic acid so as to aid in fulfilling the global demand. Oil palm including the vegetation liquor of palm oil milling offers a source of shikimic acid.

It is known that oil palm is the most important commercial crop in Malaysia and several countries in South East Asia. It has been identified that phenolic compounds extracted from oil palm exhibit diverse health benefits. Thus efforts are being made to further explore these compounds and other extracts of oil palm, including the vegetation liquor of the milling process and palm oil mill effluent (POME) for the development of functional foods, medical, nutraceutical and pharmaceutical preparations in recent times.

This invention focuses on realizing the value and potential of the vegetation liquor from palm oil milling and palm oil mill effluent (POME) as a source as shikimic acid, and further the possibility of using extracts from oil palm, the vegetation liquor from palm oil milling and POME as functional foods, medical, nutraceutical and pharmaceutical preparations.

SUMMARY OF THE INVENTION

In one embodiment, the present invention relates to a composition of at least 5 major phenolic compounds including but not confined to isomers of caffeoylshikimic acids, hydroxy benzoic acids protocatechuic acids and hydroxytyrosol from any part of oil palm, the vegetation liquor from palm oil milling and palm oil mill effluent.

In another embodiment, the present invention relates to a method for the separation and purification of a composition containing caffeoylshikimic acids and their derivatives. The said method comprises the steps of pre-concentrating an extract containing said caffeoylshikimic acids and their derivatives and then isolating said caffeoylshikimic acids and their derivatives from said extract by preparatory liquid chromatography. The elution time of the fraction containing said caffeoylshikimic acids could vary depending on the conditions of the mobile and stationary phases.

BRIEF DESCRIPTION OF THE DRAWINGS

This invention will be described by way of non-limiting embodiments of the present invention, with reference to the accompanying drawings, in which.

DETAILED DESCRIPTION

Figure 1:
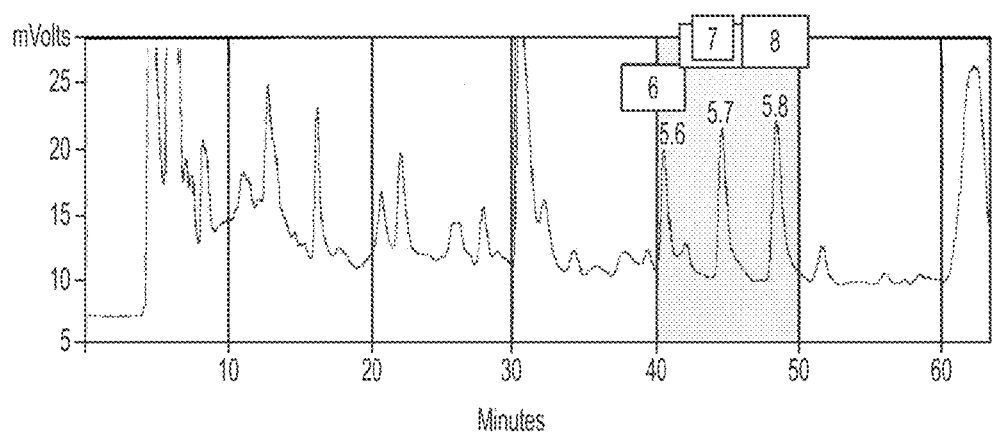
FIG. 1 shows a chromatogram containing peaks 6, 7 and 8 obtained based on an embodiment of the present invention.

In line with the above summary, the disclosed description and examples is directed to a composition, use and method thereof for use various health related purposes, in the form of treatments and/or prophylaxis of diseases using extracts of oil palm and from the vegetation liquor of the palm oil milling process.

The biologically active extracts of palm vegetation liquor useful in this invention are those obtained from the vegetation liquor of the palm oil milling process according based on, but not confined to the steps involved in the method as disclosed in US Patent Application No 20030031740.

Although the extract may contain a variety of compounds including phenolic compounds, fruit acids, fruit sugars and glycerol, starch, cellulose and hemicellulose, for purposes of standardization the concentrations of the extracts used were measured in terms of phenolic content i.e gallic acid equivalent.

Embodiments of the present invention are predicated in part on a composition comprising caffeoylshikimic acids and other major phenolic compounds obtained from any part of the oil palm including vegetation liquor of palm oil processing and palm oil mill effluent. The composition of the present invention is prepared in accordance with several steps of a method, which is another aspect of the present invention. It is expected that the preparation is safe and said composition is suitable for use in, but not limiting to, daily consumption including dietary supplements, nutraceuticals, health promoting purposes, therapeutic applications, immunostimulating, immune system enhancing, neuroprotective, anticancer, antiflammatory, antioxidant and as antiaging agents. It is further noted that the caffeoylshikimic acids and their derivatives obtained based on the preferred embodiments of the present invention is suspected to exhibit vascular protective and antidiabetic effects and to lower blood pressure.

It would be apparent to a person skilled in the art that the raw extracts obtained from any part of the oil palm, the vegetation liquor from palm oil milling and palm oil mill effluent for the purpose of the present invention may contain various other phenolic compounds in addition to primary marker compound caffeoylshikimic acids, these compounds may include hydrobenzoic acid, hydroxytyrosol, gallic acids, protocatechuic acid, 2,3-dihydroxybenzoic acid, chlorogenic acid, caffeic acid, ferulic acid, flavonoids, micronutrients and other natural plant components including cellulose and hemicellulose, starch, sugar, lipids, amino acids and proteins.

Caffeoylshikimic acids and their derivatives are found in low concentration in nature. The method of the present invention aims to provide caffeoylshikimic acids and their derviatives in substantially purified form for the preparation of the composition of the present invention.

The extracts obtained form oil palm including the vegetation liquor from palm oil milling and palm oil mill effluent when subjected to isolation and purification stages in accordance with the method of the present invention is found to contain at least one of the following compounds; hydroxytyrosol, p-hydroxybenzoic acid, 5-0-caffeoylshikimic acid, 4-0-caffeoylshikimic acid and 3-0-caffeoylshikimic acid.

The present invention extends, therefore to a method for preparation of purified caffeoylshikimic acids, whereby the primary steps of said method are pre-treatment of raw extracts obtained from any part of the oil palm, the vegetation liquor from palm oil milling and palm oil mill effluents and the isolation of caffeoylshikimic acids from said raw extracts. This embodiment encompasses isolated or substantially purified caffeoylshikimic acids. It should be noted that an "isolated" or "purified" caffeoylshikimic acid, or biologically active portion thereof, is substantially free of other cellular materials or other components or substantially free of chemical precursors or other chemicals.

The following examples serve to merely explain different methods of preparing caffeoylshikimic acids and related compounds and should not be confined thereof.

The first step of the method for preparation of the composition is pre-treatment of the raw extracts to obtain pre-concentrated or partially purified extracts. This may be performed with low stringent conditions of subjecting the extracts to a flash chromatography or the likes, or alternatively, subjecting said extracts to ethanol precipitation, prior to separation by high performance liquid chromatography. The main steps involved for the first approach is loading a "sep-pak" type column, removing impurities, eluting said extracts with methanol or ethanol and subjecting said extracts for concentration stage in a rotary evaporator. The second approach comprises the steps of adding an amount of extract to three volumes of cold ethanol, storing said mixture overnight at a preferred temperature of −20° C., centrifuging at 1500×g for at least 15 minutes, dissolving the precipitate obtained from the previous step with a suitably amount of distilled water and concentrating by rotary evaporator at 50° C. to obtain the preferred final value of 3 ml. It should be mentioned that these steps for both approaches may be substituted with alternative steps of standard procedures known in the art however to achieve a similar objective.

The next imperative step of the method for the preparation of the composition comprising caffeoylshikimic acids and their derivatives involves the isolation and purification of caffeoylshikimic acids from the partially purified extracts. This can be carried out with the conventional high performance liquid chromatography (HPLC) based on low stringent conditions or parameters of preparing an econosil C18 5 μm particle size, with the preferred column length of 25 cm×10 mm id, flow rate of 3 ml per minute. The preferred mobile phase gradient comprises two solvents, at least one solvent consisting of 0.1% trifluoroacetic acid (TFA) with an amount of water and added with another solvent consisting of 10/90 of 0-1% TFA/acetonitrile (ACN) v/v. The mixture is subjected to isolation by HPLC and it is observed that there are three major peaks indicating the elution of caffeoylshikimic acids at 40 minutes, 44 minutes and 48 minutes. The eluted caffeoylshikimic acids collected in accordance with the present invention may have within 90% to 95% or more purity. It would be understood that the choice of columns and parameters for HPLC may vary however to obtain a similar result of elution time as described. Eluted fraction may be suitably collected and provided in powder or liquid form for use in further analysis.

Further chemical analysis on determining the structure of caffeoylshikimic acids based on the peaks as obtained in accordance with the method of the present invention may be carried out based on conventional or standard procedures known in the art, for instance based on well known the Nuclear Magnetic Resonance (NMR) analysis.

The method of the present invention may be carried out to isolate and purify caffeoylshikimic acids and their derivatives from any plant or type of sources, including, but not limited to dates (fruits of *Phenix reclinata*), olive (*Olea europaea*), oats, barley, safflower, fruits, vegetables, juices, coconut (*Cocos nucifera*), corn (*Zea mays*), seeds, wastes, and tissues obtained from plants.

The present invention is further described in the following non-limiting Examples.

EXAMPLES

Example 1

Isolation and Pretreatment

Extract from oil palm, vegetation liquor from palm oil milling and palm oil mill effluent was prepared based on a filtration procedure.
Pre-Concentration Treatment The sample was pre-concentrated with Sample Prep using "Sep pak" cartridges for solvent exchange. The selected chromatography used to concentrate the sample was preparative high performance liquid chromatography (HPLC).

The solvent exchange was carried out based on the following steps:
 a) Conditioning—involving the flushing the unused separation pack (C18) with methanol and subsequently with water.

b) Sample Injection—involving injecting an amount of 2 ml of sample into the separation pack and then forced out with a suitable syringe.

c) Washing—involving injecting 1 ml of water through the pack to remove any form of impurities from the sample.

d) Eluting—involving injecting 2 ml of methanol through the separation pack so as to elute the remaining sample which had not been eliminated during the previous washing stage.

In the next step, the eluted sample as concentrated three (3) fold using nitrogen. The clear sample was then injected into the semi-prep column.

Semi-Prep High Performance Liquid Chromatography (HPLC)

The preferred column was C18 column with the length of 25 cm and Id of 10 mm, used with a flow rate of 3 ml/min. In this study, the injection column was 1 ml and readings were taken at 280 nm. The mobile phase gradient is shown below in TABLE 1:

| Time (minutes) | Solvent A (0.1% TFA) | Solvent B (Methanol) |
|---|---|---|
| 0 | 90 | 10 |
| 1 | 90 | 10 |
| 55 | 60 | 40 |
| 60 | 0 | 40 |
| 65 | 0 | 100 |
| 70 | 90 | 10 |

Peak Isolation

A chromatogram obtained from the injection of concentrated sample is as shown in FIG. 1. The sample is seen to elute at 40 minutes, 44 minutes and 48 minutes thereby resulting to peaks 6, 7, and 8. Each eluted fraction was then freeze-dried, whereby 1.8 mg, 1.6 mg and 1, 1 mg of dry sample were obtained from peaks 6, 7 and 8 respectively.

Figure 2A:
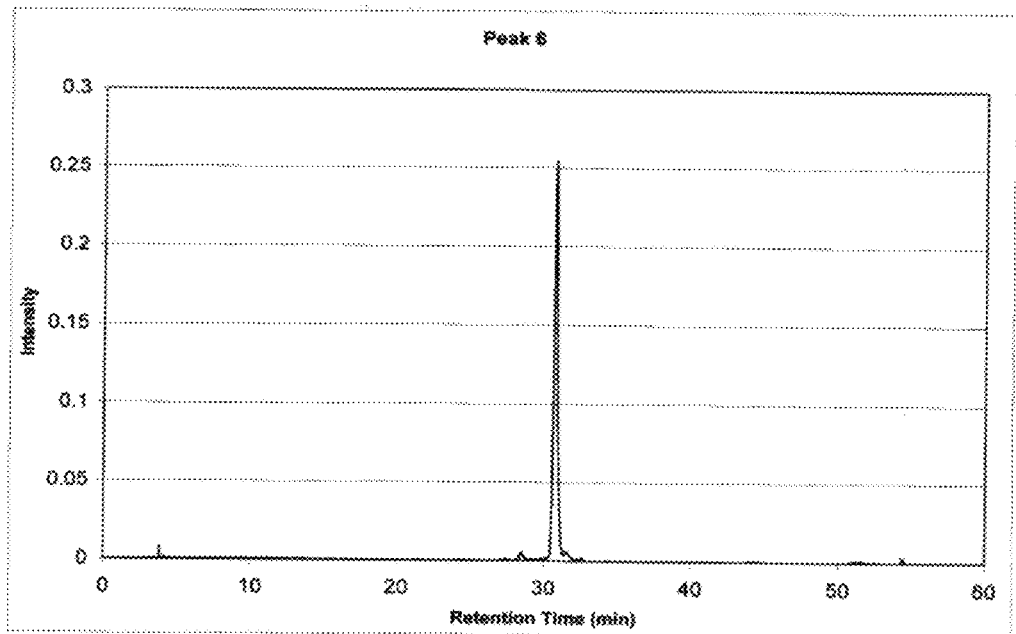
FIG. 2 (a) to FIG. 2 (c) show the analytical chromatogram for peaks 6, 7 and 8 respectively obtained based on an embodiment of the present invention.
Figure 2B:
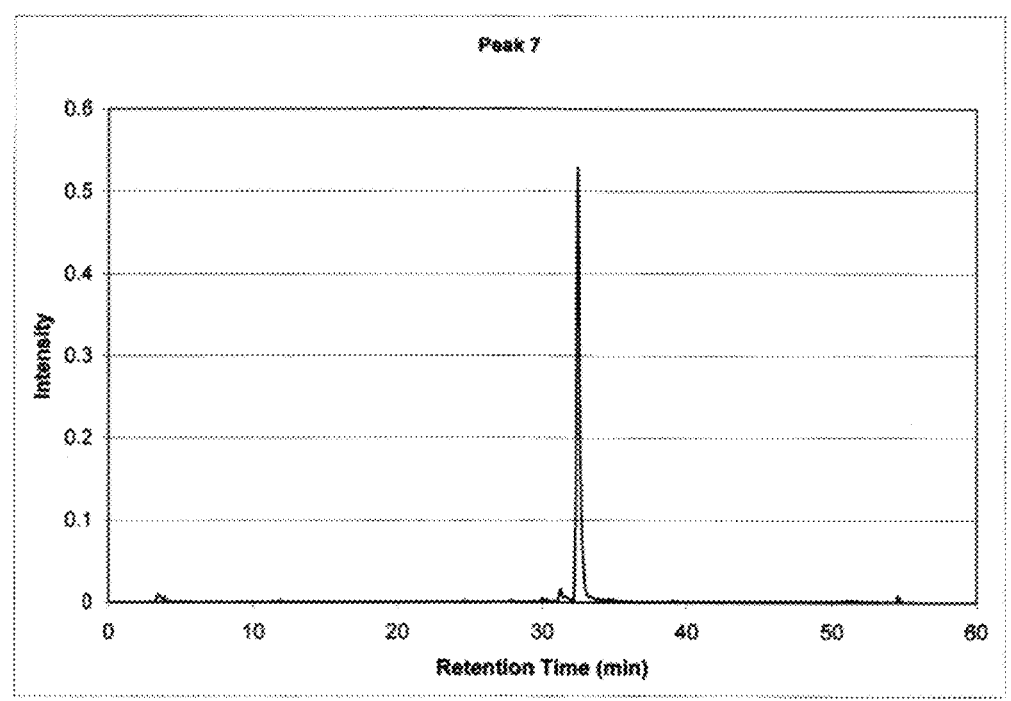
Figure 2:
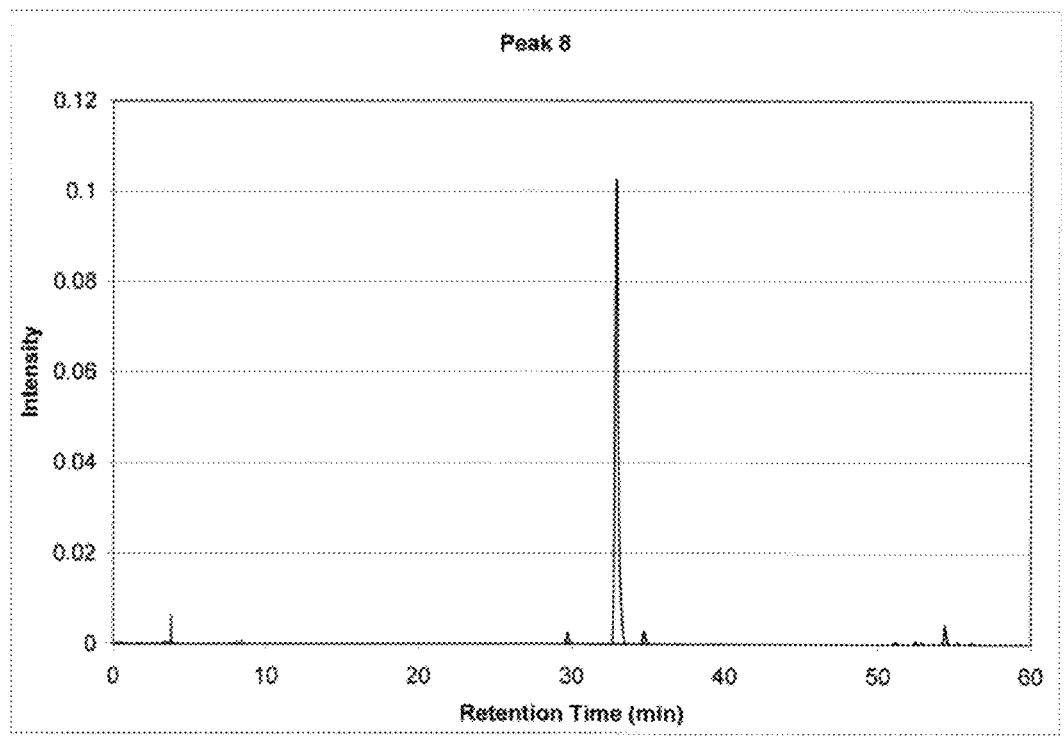

In the next step, the purities of the peaks were further analysed through Analytical HPLC, at which it was observed that the purity of the peaks is better than 95%. FIG. 2(a) to (c) provides the analytical chromatograms for peak 6, 7, and 8 respectively.

Example 2

Chemical Structure of Peaks

Figure 3:
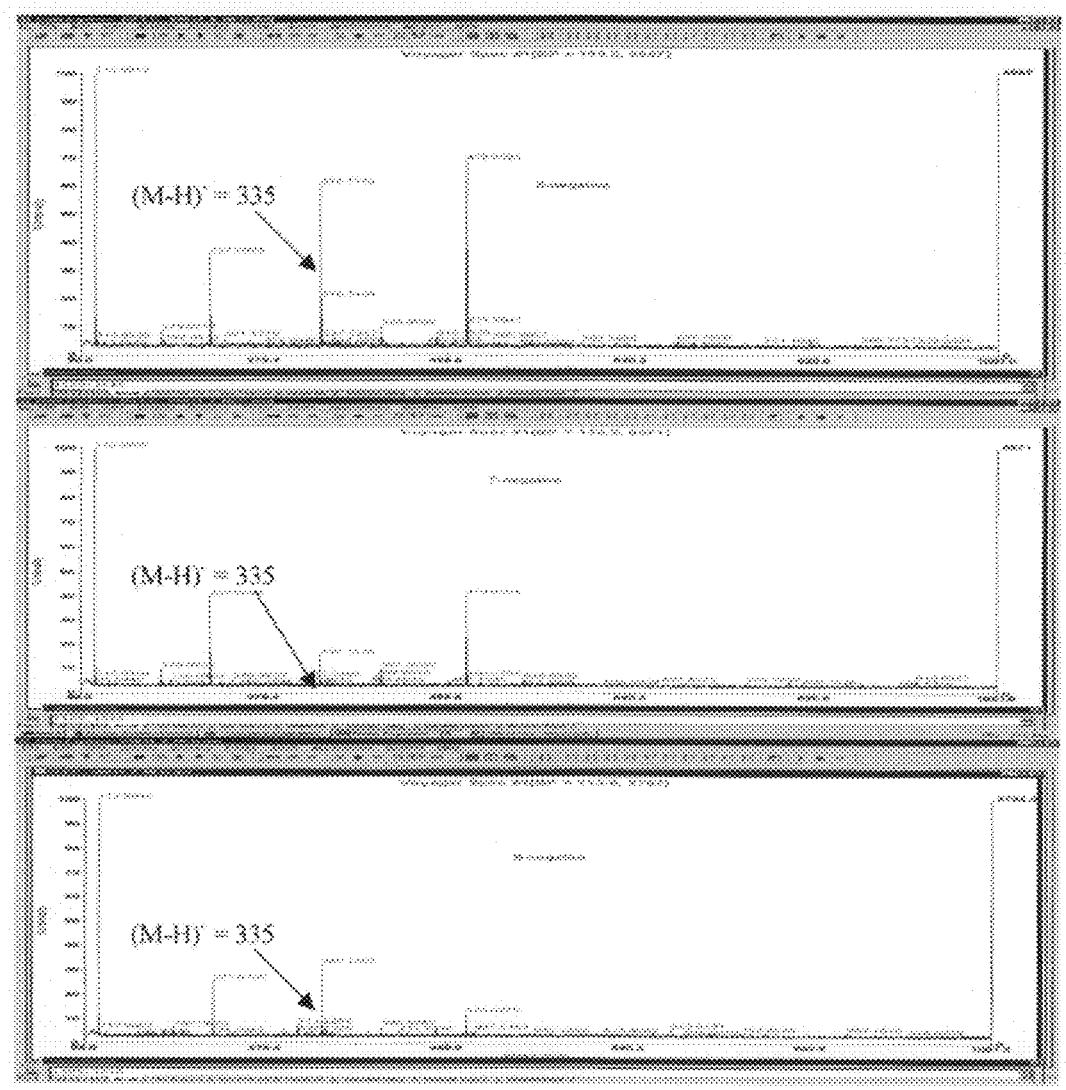
FIG. 3 shows the MALDI spectra of peaks 6, 7 and 8.

The molecular weights of the three peaks obtained can be obtained using MALDI Mass Spectra analysis. An amount of 1 µl of the sample was directly deposited onto the sample holder to determined (M-H). Results obtained from this analysis are shown in FIG. 3.

Figure 4:
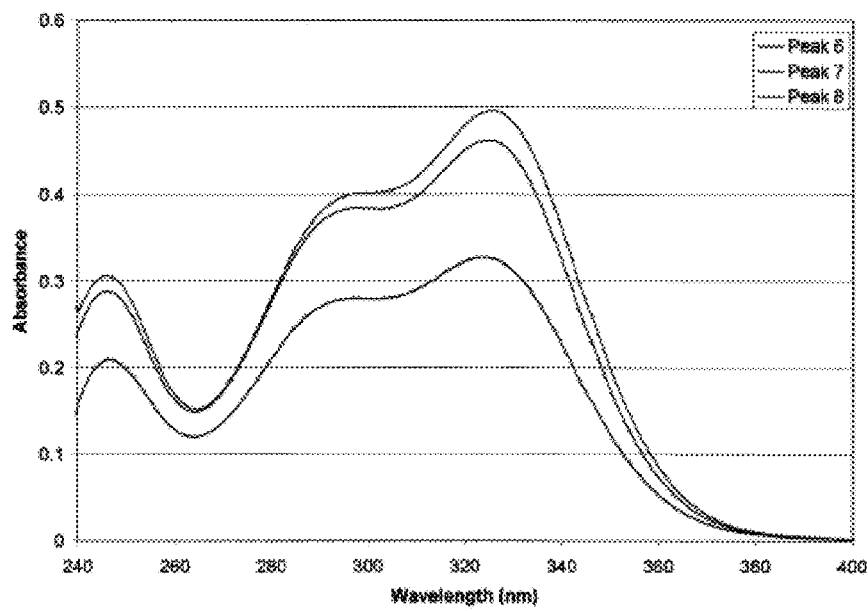
FIG. 4 shows the UV spectra for peaks 6, 7 and 8.

The UV spectrums of peaks 6, 7 and 8 were taken and it is found that the UV spectrums for all these compounds were similar, as suitably shown in FIG. 4.

NMR Analysis

Figure 5:
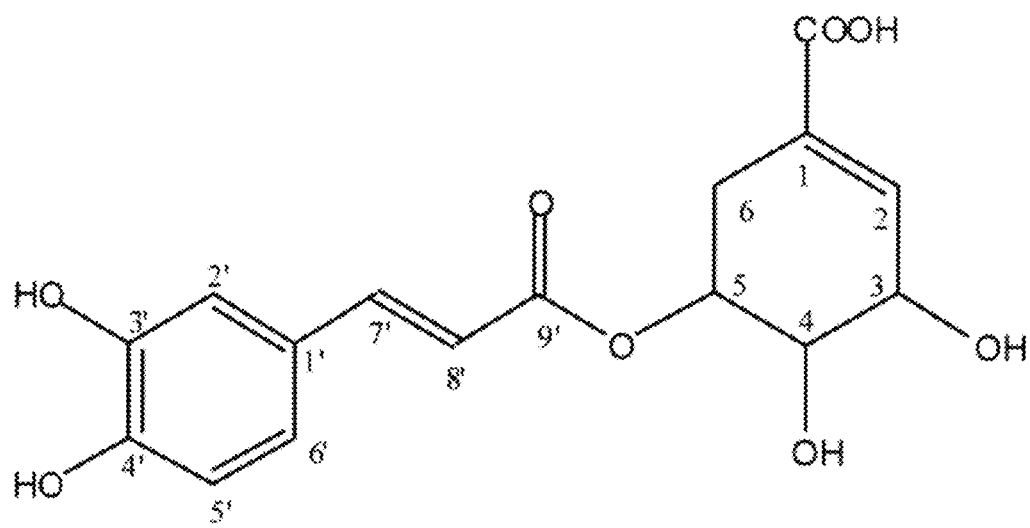
FIG. 5 shows caffeoylshikimic acid, or a 3,4-dihydroxycinnamoyl ester of shikimic acid.

The chemical structure of the compound based on these peaks was analysed using NMR analysis. Results obtained indicate that each molecule from peaks 6, 7 and 8 has 16 carbons with two carbonyls (ester or carboxyl) ten sp2 carbons whereby one aromatic ring with another two double bonds, three oxygenated methine carbons and a methylene carbon. It is further observed that the aliphatic protons in the molecule are in two spin systems. The chemical shifts of the carbons and the associated protons thereby indicate the structure of caffeoylshikimic acid, also known as 3,4-dihydroxycinnamoyl ester of shikimic acid. This can be seen in FIG. 5.

Figure 6:
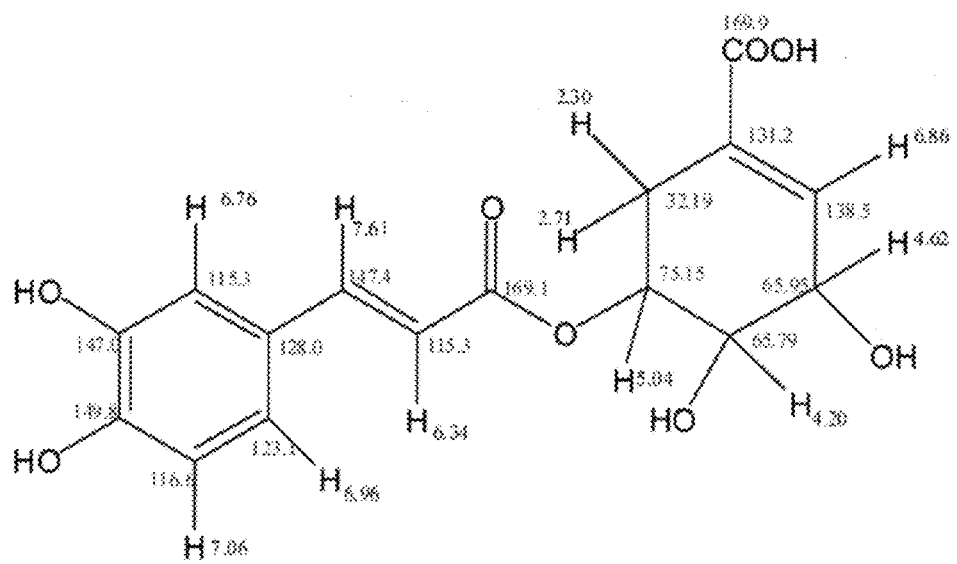
FIG. 6 shows the carbon and proton chemical shifts.
Figure 7:
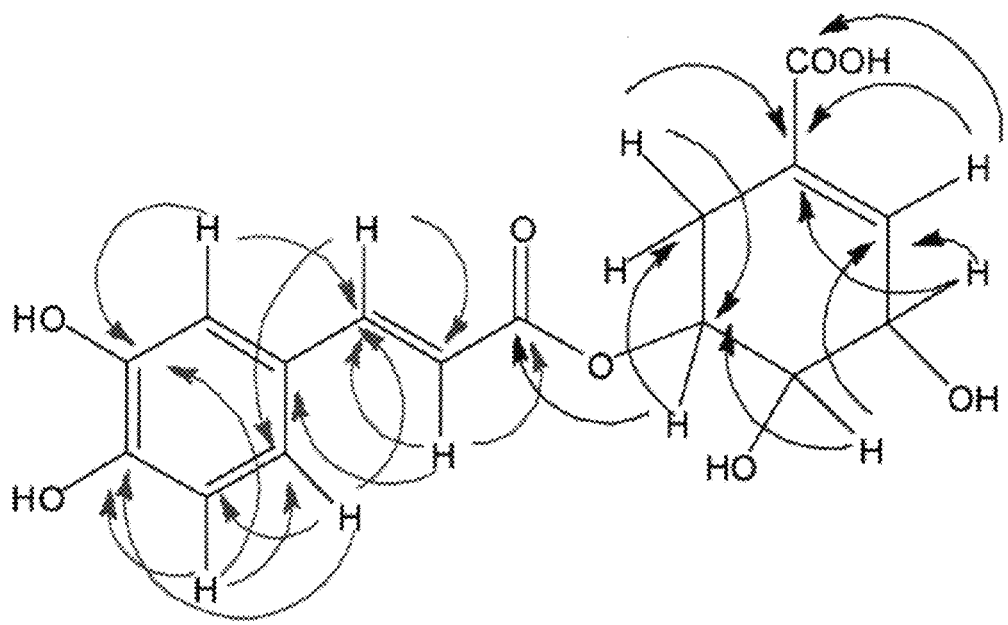
FIG. 7 shows the selected HMBC correlations.

It is recorded that the compound has a molecular mass of 336, as confirmed by a prominent peak at (M-H)=335 in its mass spectrum. Hetero-nuclear multiple bond correlation (HMBC) provides extensive two and three C—H correlations thereby confirming the structure as shown in FIG. 6 and FIG. 7.

The confirm structure of peak 6 is 5-O-caffeoylshikimic acid ($C_{16}H_{16}O_8$) with a molecular mass of 336. The identified compound and two positional isomers of caffeoylshikimic acid (3-O-caffeoylshikimic acid and 4-O-caffeoylshikimic acid) can be found in date fruits. Those skilled in the art would be able to determine that these compounds may be formed by the dehydration of the analogous 5-O-caffeoylquinic acid.

Example 3

Profiling—Reverse Phase HPLC

Figure 8:
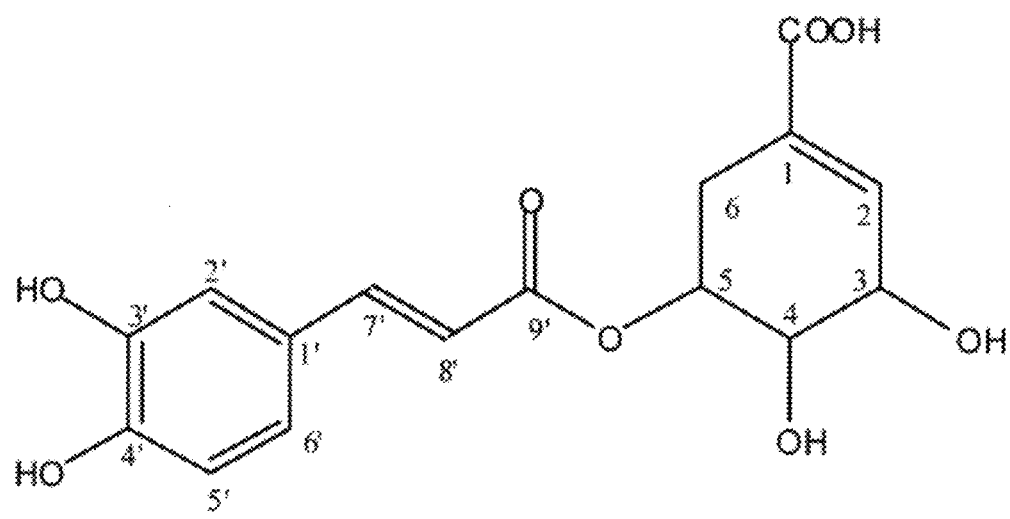
FIG. 8 shows the marker compounds.
Figure 8:
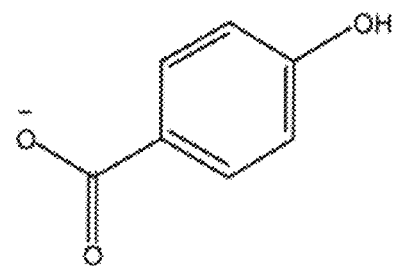
Figure 8:
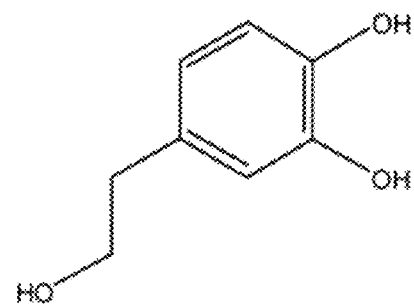

As shown in FIG. 8, the sample contains at least one of the following compounds, hydroxytyrosol, protocatechuic acid, p-hydroxybenzoic acid, 5-0-caffeoylshikimic acid, 4-0-caffeoylshikimic acid and 3-0-caffeoylshikimic acid.

In order to carry out further HPLC analysis on the compounds, the sample was prepared as follows:

a) Preparing 10 mg of alpha-cyano-4-hydroxycinnamic acid, 99% was added to 1 ml of ethanol;

b) The internal standard solution (20 µl) was added to 980 µl of the sample; and c) 300 µl of this mixture was used for HPLC analysis.

A reverse phase HPLC was conducted based on the above conditions whereby an Exsil ODS 5 µm SGE column (250×4.6) was used with a flow rate of 0-8 ml/min and a photodiode detection of 280 nm. The injection volume was 20 µl. The mobile phase gradient for this analysis is shown below in TABLE 2 below:

| Time (minutes) | Solvent A (0.1% HOAC) | Solvent B (10% water/ACN V/V) |
|---|---|---|
| 0 | 100 | 0 |
| 10 | 95 | 5 |
| 45 | 70 | 30 |
| 50 | 0 | 100 |
| 55 | 0 | 100 |
| 60 | 100 | 0 |

Figure 9:
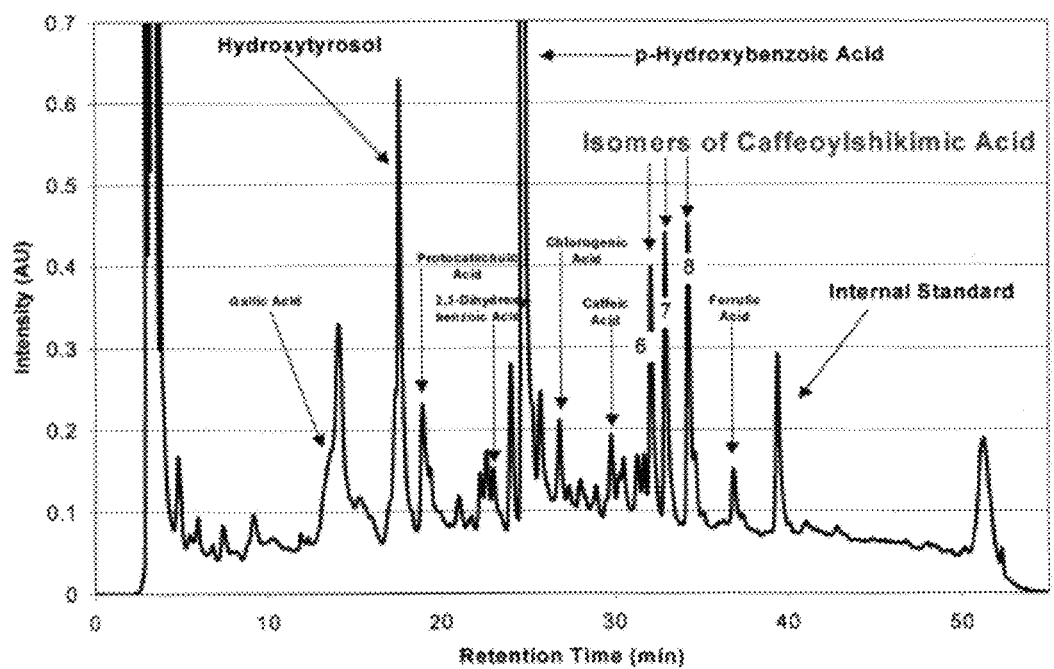
FIG. 9 shows the HPLC profile (fingerprint) of the composition.

FIG. 9 shows the chromatogram of the sample, whereby it can be seen that there are 5 major peaks, indicating the presence of hydroxytyrosol, protocatechuic acid, p-hydroxybenzoic acid and three isomers of caffeoylshikimic acid, amongst the minor peaks representing several other phenolic compounds including gallic acid, ferulic acid, and etc.

It is further observed that the minor peaks may account for at least 20% of the phenolics of the sample. Accordingly, the major peaks were substantially accounted for the quantitation of the phenolics content for the sample. The standard used for this study was alpha-cyanohydroxycinnamic acid with the retention time of 39 minutes for quantitation.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention claimed is:

1. A method for preparing a composition comprising caffeoylshikimic acids and their derivatives, said method comprising:
   providing an extract from any part of oil palm;
   pre-concentrating said extract containing said caffeoylshikimic acids and their derivatives; and
   isolating said caffeoylshikimic acids and their derivatives from said extract by high performance liquid chromatography (HPLC) with a C18 column with 25 length and 10 mm id, using at least one solvent containing 0.1% trifluoroacetic acid and another solvent containing 10/90 0.1% trifluoroacetic acid per acetonitrile for mobile phase gradient, wherein the elution activity of said caffeoylshikimic acids and their derivatives results in a plurality of peaks on said liquid chromatography; wherein the elution activity occurs at 40, 44 and 48 minutes within at least one fraction of the extract, thereby producing at least three peaks by said liquid chromatography.

2. The method of claim 1, wherein the pre-concentrating step further comprises:
   loading a column with the extract,
   removing the impurities,
   eluting the extract with methanol or ethanol,
   concentrating in a rotary evaporator,
   adding an amount of cold ethanol, storing at −20° C., centrifuging said mixture, dissolving the precipitate obtained from centrifuging with an amount of water and concentrating said mixture by rotary evaporator at 50° C.

3. The method of claim 2, wherein the amount of cold ethanol is at least 3 volumes of the extract.

4. The method of claim 2, wherein the amount of water for dissolving the precipitate is approximately 10 ml.

5. The method of claim 1, wherein the percentage of purity of the caffeoylshikimic acids and their derivatives obtained upon isolated is within 90 to 95%.

* * * * *